(12) United States Patent
Jawarski et al.

(10) Patent No.: US 12,216,107 B2
(45) Date of Patent: Feb. 4, 2025

(54) CONCRETE WORKABILITY METER

(71) Applicant: MINNICH MANUFACTURING COMPANY, inc., Mansfield, OH (US)

(72) Inventors: Paul Jawarski, Shorwood, IL (US); Allen Bragg, Ashland, OH (US); Tobin Pokrzywa, Ashland, OH (US); Jeff McDaniel, Ashland, OH (US)

(73) Assignee: MINNICH MANUFACTURING COMPANY, INC., Mansfield, OH (US)

( * ) Notice: Subject to any disclaimer, the term of this patent is extended or adjusted under 35 U.S.C. 154(b) by 312 days.

(21) Appl. No.: 17/806,855

(22) Filed: Jun. 14, 2022

(65) Prior Publication Data
US 2022/0397563 A1  Dec. 15, 2022

Related U.S. Application Data

(60) Provisional application No. 63/210,264, filed on Jun. 14, 2021.

(51) Int. Cl.
*G01N 33/38* (2006.01)

(52) U.S. Cl.
CPC ................... *G01N 33/383* (2013.01)

(58) Field of Classification Search
CPC .................................................. G01N 33/383
See application file for complete search history.

(56) References Cited

U.S. PATENT DOCUMENTS

| | | |
|---|---|---|
| 3,021,442 A | 2/1962 | Rodak |
| 3,549,130 A | 12/1970 | Briggs |
| 4,171,190 A | 10/1979 | Hudson |
| 5,126,607 A | 6/1992 | Merriman, Jr. |
| 5,202,612 A | 4/1993 | Yoshida et al. |
| D622,215 S | 8/2010 | Heimbruch et al. |
| 2002/0152570 A1 | 10/2002 | Hohlbein |
| 2004/0022581 A1 | 2/2004 | Corbitt |
| 2004/0159073 A1* | 8/2004 | Palermo ................ C04B 41/72 52/745.19 |
| 2005/0276156 A1 | 12/2005 | Elsten |
| 2007/0167885 A1 | 7/2007 | Moon |
| 2007/0201302 A1 | 8/2007 | Lindley |
| 2007/0268128 A1 | 11/2007 | Swanson et al. |
| 2012/0092948 A1 | 4/2012 | Heimbruch et al. |
| 2016/0223511 A1* | 8/2016 | Koshnick ............ A01C 21/007 |
| 2016/0365769 A1 | 12/2016 | Raczek et al. |
| 2017/0126100 A1 | 5/2017 | Chou |
| 2018/0059060 A1* | 3/2018 | Dusseault ............ G01N 33/383 |

(Continued)

OTHER PUBLICATIONS

International Search Report and Written Opinion mail date Apr. 30, 2019 from International Application No. PCT/US2019/012080, International Filing Date Jan. 2, 2019. Authorized officer Blaine R. Copenheaver. 19 pages.

(Continued)

*Primary Examiner* — Peter J Macchiarolo
*Assistant Examiner* — John M Royston
(74) *Attorney, Agent, or Firm* — Vorys, Sater, Seymour and Pease LLP; Mark A Watkins

(57) ABSTRACT

A concrete workability meter having concrete vibrator portion and frame assembly, wherein the concrete vibrator portion may be selectively decoupled from the frame assembly to permit relative movement there between.

19 Claims, 9 Drawing Sheets

(56) References Cited

U.S. PATENT DOCUMENTS

| | | | | |
|---|---|---|---|---|
| 2018/0282788 | A1* | 10/2018 | Opalsky | G01N 35/1009 |
| 2019/0207465 | A1* | 7/2019 | Jaworski | H02K 5/14 |
| 2020/0096251 | A1* | 3/2020 | Costanza | E04B 1/6125 |
| 2022/0173688 | A1* | 6/2022 | Smith | B64D 31/00 |

OTHER PUBLICATIONS

Wyco, 995 Electric Motor Vibrator, printed Apr. 2, 2019, 6 pages, https://www.badgermeter.com/business-lines/wyco/995-electric-motor-vibrator/.

Oztec, Concrete Vibrating Motors—Electric, printed Apr. 2, 2019, 1 page, www.oztec.com/electric_power_units.htm.

Multiquip, Flex-Shaft Vibrators, printed Apr. 2, 2019, 4 pages, www.multiquip.com/multiquip/flex-shaft-vibrators.htm.

Northrock Industries, Electric Vibrators, printed Apr. 2, 2019, 3 pages, www.northrockindustries.com/ElectricVibrators.

Wyco, Sure Speed 2.0 Electric Motor Vibrator—Badger Meter, printed Apr. 2, 2019, 7 pages, https://www.badgermeter.com/business-lines/wyco/sure-speed-20-electric-motor-vibrator/.

Wacker Neuson HMS, Modular Internal Vibrators for More Flexibility, printed Apr. 2, 2019, 2 pages, https://www.wackerneuson.us/en/products/concrete-technology/internal-vibrators/basic-line-internal-vibrators/.

Wyco, Flex Shaft Concrete Vibrators User Manual, Sure Speed 2.0 and 995, VBR-UM-02653-EN-02 (May 2018), 20 pages.

Multiquip, Operation and Parts Manual, Models CV1A, CV2A/2B, CV3A/3B Vibrator Motor, Revision #1 (Apr. 9, 2018), 34 pages.

Minnich, Flex Shaft Vibrators, Electric and Gasoline, 2015 Brochure, 4 pages.

Wyco Tool, Sure Speed Concrete Vibrator, Construction Equipment Brochure, Sep. 28, 2010, printed Apr. 2, 2019, 4 pages, https://www.constructionequipment.com/wyco-tool-sure-speed-concrete-vibrator.

* cited by examiner

CONCRETE WORKABILITY METER

BACKGROUND

This application claims priority benefit of U.S. Provisional Patent Application Ser. No. 63/210,264 filed Jun. 14, 2021, entitled "Concrete Workability Meter," the complete disclosure of which, in its entirety is herein incorporated by reference.

BACKGROUND

Workability of concrete is a poorly defined property that has long been a challenge to predict and measure. Over the years, test procedures have been developed to determine workability for research, mix proportioning, and field use. One such test is the Kelly ball test, which was developed as an efficient alternative to the slump test. The Kelly ball test utilizes an apparatus having a ball attached to a graduated shaft/stem, wherein the ball is placed on a recently poured concrete surface and penetration of the ball into the concrete surface is measured via the measurements on the shaft/stem.

The vibrating Kelly ball test ("VKelly") utilizes an apparatus having a ball attached to a vibrator. Not only may the VKelly apparatus be utilized to test concrete statically, e.g., via the Kelly ball test by releasing the ball onto the prepared surface of the concrete and measuring its penetration, but the VKelly apparatus may also test the concrete dynamically. For example, a test procedure for utilizing the VKelly apparatus may include turning on the vibrator and record penetration of the ball over time, e.g., in 6 second intervals for up to 36 seconds. Sometimes, a video recorder is utilized to record the test such that the collected test data may analyzed at a later time.

Current test equipment, however, is imprecise and requires careful practice to ensure accurate results. Accordingly, a need exists for improved concrete workability testing equipment.

SUMMARY

Various details of the present disclosure are hereinafter summarized to provide a basic understanding. This summary is not an extensive overview of the disclosure and is intended neither to identify certain elements of the disclosure, nor to delineate the scope thereof. Rather, the primary purpose of this summary is to present some concepts of the disclosure in a simplified form prior to the more detailed description that is presented hereinafter.

In accordance with one aspect of the present disclosure, a concrete workability meter is described. A concrete workability meter assembly includes a testing assembly including a concrete testing instrument operatively connected to a vibrator and a frame assembly configured to slidingly support the testing assembly. In a further embodiment, the vibrator includes a variable speed motor and is controllable to manipulate the testing instrument. In another further embodiment, the assembly further includes a shaft extending between the vibrator and testing instrument, the shaft configured to transfer vibrating energy from vibrator to the testing instrument. In another further embodiment, the testing instrument is a ball. In another further embodiment, the frame assembly includes a slider plate configured to permit relative sliding between the slider plate and the vibrator. In another further embodiment, the slider plate includes a central bore includes least one notch configured to receive a correspondingly shaped at least one tab portion positioned vertically along the vibrator, the at least one tab portion and notch configured to provide alignment and guided movement between the vibrator and slider plate. In another further embodiment, the assembly includes a cage assembly that shrouds a motor of the vibrator. In another further embodiment, the cage assembly includes a pair of endcaps and at least one handle extending therebetween wherein the at least one handle is isolated from vibrations. In another further embodiment, the frame assembly includes a slider plate configured to permit relative sliding between the slider plate and the vibrator, the slider plate includes a plurality of apertures sized and placed to retain at least a portion of the testing assembly. In another further embodiment, the frame assembly includes a locking system capable of having an engaged position that locks the testing assembly to the frame assembly and a disengaged position that allows sliding movement of the testing assembly relative to the frame assembly. In another further embodiment, the locking system includes a hook configured to couple the vibrator and the frame assembly relative to one another. In another further embodiment, the frame assembly includes a plurality of legs rotatably and adjustably coupled to a slider plate. In another further embodiment, the frame assembly includes an elongated central frame member that extends between a handle bar and base. In another further embodiment, the assembly further includes at least two wheels axially coupled to the elongated central frame member proximate to the base. In another further embodiment, the frame assembly includes a shaft guide having an end portion configured to slidingly engage a shaft that connects the vibrator to the testing instrument. In another further embodiment, the vibrator generates an electrical load impedance curve from a looping circuit.

In accordance with another aspect of the present disclosure, a method of testing concrete workability is described. The method includes providing a testing apparatus having a concrete vibrator portion and frame assembly, and decoupling the concrete vibrator portion from the frame assembly to permit relative movement there between. In a further embodiment, the step of de-coupling includes removing a pin from a hook assembly and articulating a hook into a disengaged position. In another further embodiment, the testing apparatus includes a vibrating source that develops an electrical load impedance curve from a looping circuit in a PC Board of the vibrating source.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
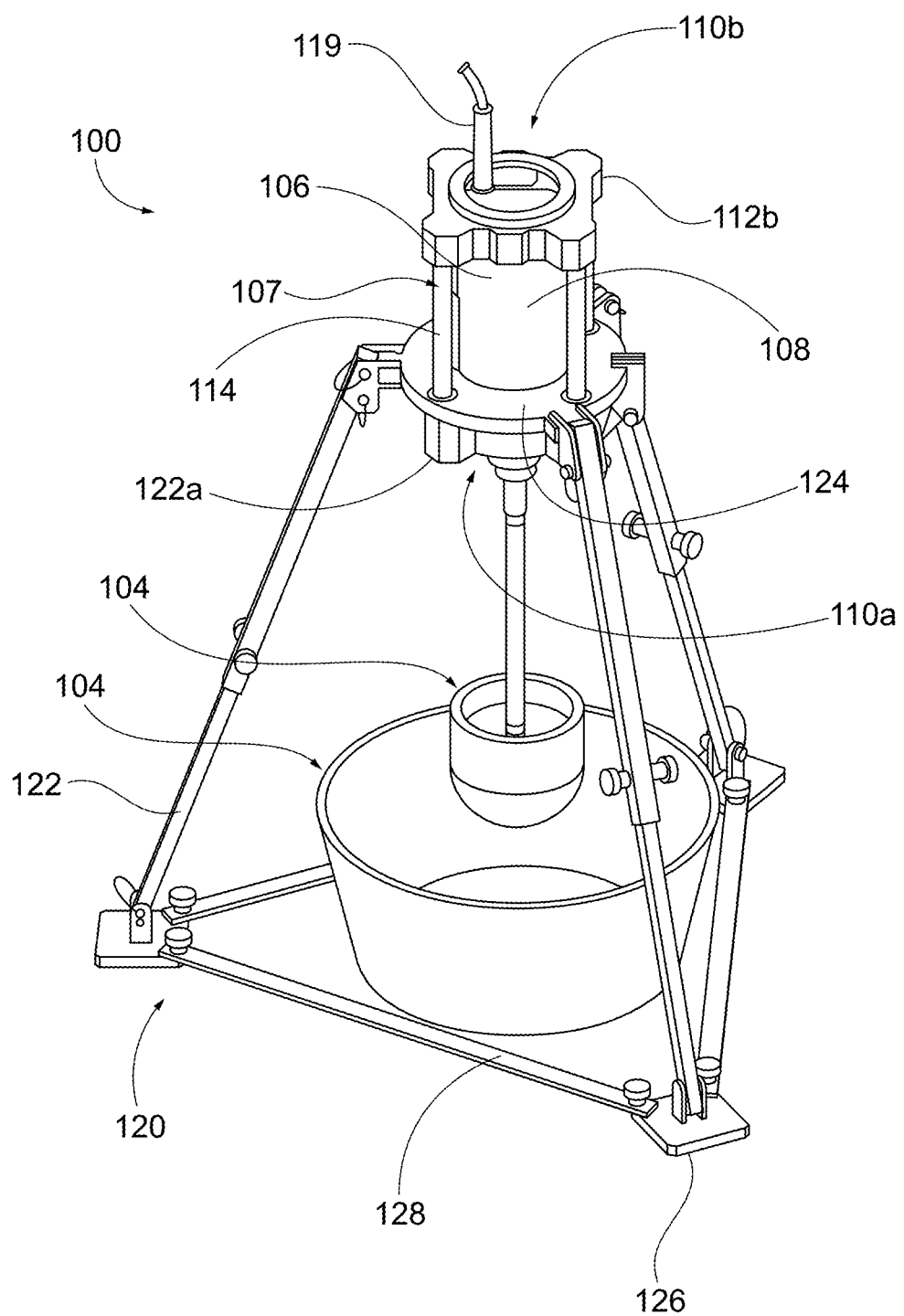
FIG. 1 is an isometric view of a concrete workability meter that may incorporate the principles of the present disclosure.

The present disclosure is related to concrete testing equipment for concrete and, more particularly, to equipment for measuring workability of concrete mixtures.

PCT Patent Application No. PCT/US2019/012080, published as WO/2019/136088A1 describes a concrete vibrator system includes a concrete vibrator having a motor, a vibratory head that is actuated by the motor, and a controller that controls the motor. A Workability Test for Slip Formed Concrete Pavements. Construction and Building Materials; M Cook, T. Ley, and A. Ghaeezadah; 2014 describes testing methods to measure the response of the concrete to vibration and the ability of the concrete to hold an edge. AASHTO TP 129 Vibrating Kelly Ball Test 2018 describes a Standard Method of Test for Vibrating Kelly Ball. Development and Evaluation of Vibrating Kelly Ball Test (VKelly Test) for the Workability of Concrete. National Concrete Pavement Technology Center. Final Report FHWA DTFH61-06-H-00011. Peter Taylor, Xuhao Wang, Xin Wang; 2015 describes a workability test method (Vibrating Kelly Ball or VKelly test) that quantitatively assess the responsiveness of a dry concrete mixture to vibration. Powers, T. C., and Wiler, E. M. (1941). "A device for studying the workability of concrete." Proceedings of the ASTM 41, American Society of Testing and Materials, Philadelphia, PA describes devices for studying the workability of concrete. Wong S, Alexander M, Haskins R, Pool T, Maloone P, Wakeley L. Portland-Cement Concrete Rheology and Workability: Final Report. FHWA-RD-00-025. Washington, DC: FHWA; 2001 is a report detailing a simple, practical test for determining the workability of freshly mixed concrete. Developing Performance Engineered Concrete Pavement Mixtures; AASHTO PP84-17 Tech Section; 3c April 2017 is a tech brief that explains how concrete paving mixtures can be engineered to meet performance requirements and how to incorporate key performance parameters into a robust specification and quality process. Effects of Aggregate Concepts on the Workability of Slip Form Concrete; M. D. Cook PhD, M. T. Ley PhD, P. E., and Ashkan Ghaeezadah; 2016 relates to workability of concrete. Investigation of Concrete Workability through Characterization of Aggregate Gradation in Harden Concrete using X-ray Computed Tomography; Ghaazal Sokhansefat, M Tyler Ley, Marlton D. Cook, Riyadh Alturki, Masoud Moradian; OkSU; 2015 is a study of aggregate packing in concrete and the workability of concrete mixtures. *Iowa DOT Research technical reports MLR-97-02; MLR-95-10; HR-1065; MLR-07-01;* J. K. Cable, L. Mc Daniels; R. Steffes; Shane Tymkowicz; 1997 also relate to the workability and study of concrete. The disclosures of each of the above are incorporated by reference herein in their entireties.

The embodiments described herein provide a testing apparatus or device for measuring workability of concrete. The testing device may be configured to run or perform concrete workability tests. In some examples, the device includes a vibrating source that develops an electrical load impedance curve from the source's looping circuit in the device's PC Board, which is reportable on a remove device, such as a smart phone, or tablet computer, which may include software for displaying and logging such data. The reported impedance curve differentials may be represented as workability curve signatures to correlate the concrete's workability variance values through the construction practices from the mixture's lab design, to batching, to transport, to pumping and eventually vibration during placement practices. The changes in the curve signatures during these concrete processes may be illustrated by the curve distortion or changes in the concrete's workability. Advantages of the device include that ability to identify and track process variability accurately utilizing well-defined and accurate indexing system, and generally providing a more predictive model than the simple and inaccurate slump cone test (ASTM C 143 or AASHTO T 119) that is prone to test administration and interpretation errors by the quality control technician.

FIG. 1 is an isometric view of an example concrete workability testing apparatus 100 that may incorporate the principles of the present disclosure. The depicted concrete workability testing apparatus 100 (hereinafter, testing apparatus 100) is just one example testing apparatus that can suitably incorporate the principles of the present disclosure. Indeed, many alternative designs and configurations of the testing apparatus 100 may be employed, without departing from the scope of this disclosure. The testing apparatus 100 is configured for taking, recording, and analyzing measurements of concrete mixtures, which may be provided or poured for testing into a container 102. However, the testing apparatus 100 may be utilized on actual concrete pours.

The testing apparatus 100 includes a VKelly instrument 104 (i.e., an instrument or ball for a VKelly ball test) operatively connected to a vibrator 106. As further described herein, the vibrator 106 includes a variable speed motor and is controllable to manipulate the VKelly instrument 104 to thereby conduct or perform a VKelly ball test or otherwise measure a property of poured concrete.

In the illustrated example, the vibrator 106 includes a cage assembly 107 that surrounds or shrouds a motor assembly 108 of the vibrator 106. As illustrated, the cage assembly 107 is a protective cage that at least partially surrounds the motor assembly 108 and encapsulates it to protect from shock. The cage assembly 107 to also provide a handle 114, discussed in detail below, which is isolated from electrical shock and vibration. Moreover, when the cage assembly 107 is tightened (i.e., the endcaps tightened onto the handle tubes) onto the motor assembly 108, it creates a seal to inhibit water ingression into the motor assembly 108. The endcaps 112a,b may fasten to handles 114 via a fastener (not illustrated) or the like. While not illustrated, an arm or shoulder strap may be provided on the concrete vibrator 106, for example, on the motor assembly 108 and/or on the cage assembly 107, and the strap may be configured as a rigid handle type structure or configured as a non-rigid tether.

In the illustrated embodiment, the cage assembly 107 includes a pair of endcaps 112a,112b and a plurality of handles 114 that extend between the endcaps 112a,112b. As described herein, the endcaps 112a,112b are configured to isolate the motor assembly 108 and the VKelly instrumentation 104 of the vibrator 106 from the rest of the testing apparatus 100.

Figure 2:
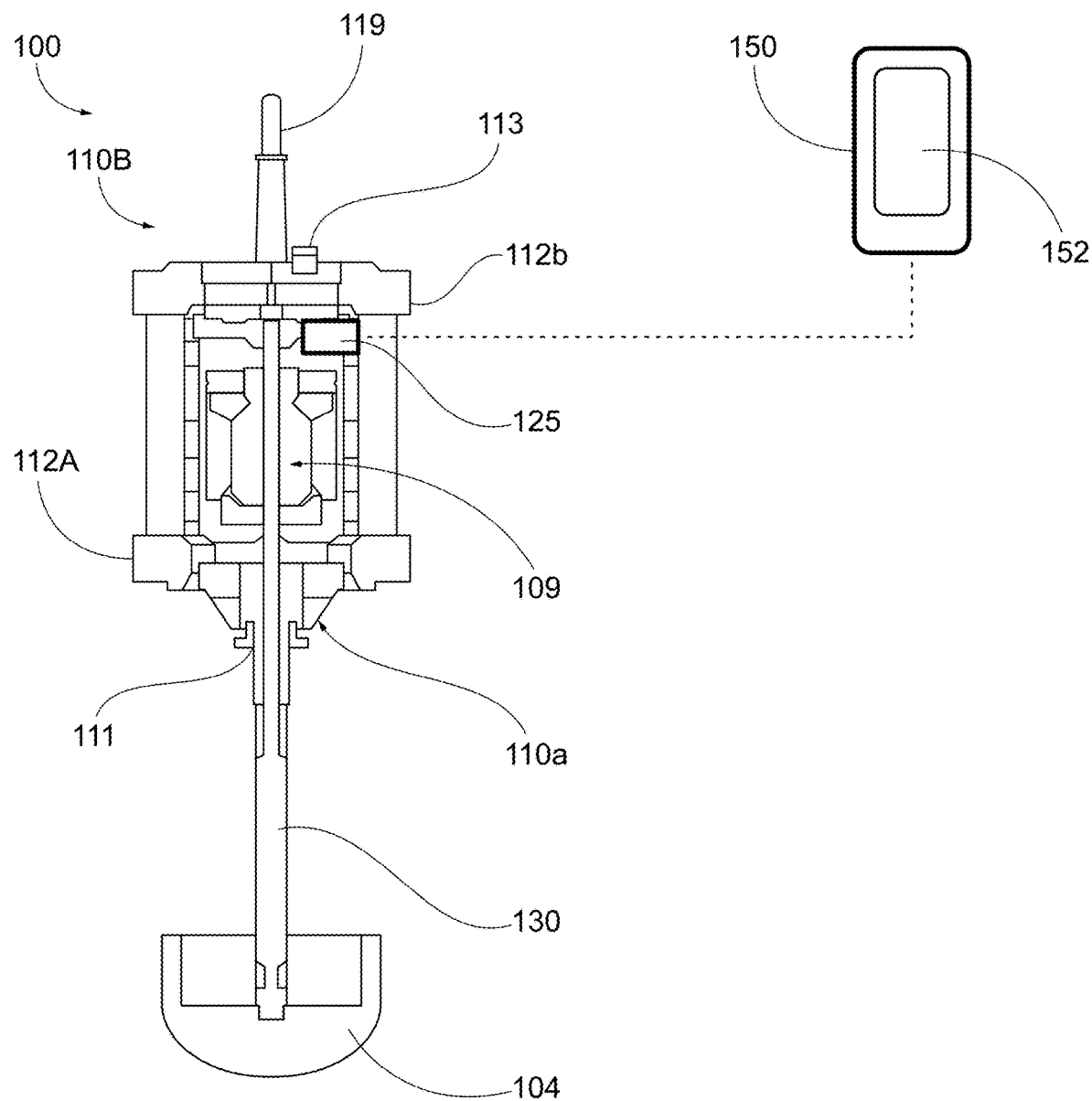
FIG. 2 is a cross-sectional side view of the concrete workability meter of FIG. 1.

FIG. 2 illustrates a cross-sectional side view of the vibrator 106 and VKelly instrument 104, according to one or more embodiments of the present disclosure. A motor pod 109 is provided within a housing of the motor assembly 108 via a plurality of brushes (not illustrated). The motor assembly 108 has a front end 110a and a rear end 110b, and an input 111 disposed proximate to the front end 110a and configured to operatively receive a shaft 130 to which the VKelly instrument 104 ball is connected. An operator of the concrete vibrator 100 may then actuate the motor pod to drive the shaft 130 such that the VKelly instrument 104 imparts vibration to a batch of concrete, for example, when the vibratory head of VKelly instrument 104 is arranged on or in the concrete mixture provided in the container 102.

The motor assembly 108 further includes a user interface 113 that is in communication with the motor pod 109. In some embodiments, a user interface 113 is arranged on the rear end 110*b* of the motor housing 108, however, it may be differently provided about the motor housing 108. In some embodiments, a user interface is provided on a remove device 150, such as a smart phone or tablet device, in addition to or in lieu of on the motor assembly 108. The remote device may be in communication with a PC Board 125 configured to operate and control the operation of the vibrator 100. An operator may control the concrete vibrator 100 via the user interface(s). Thus, the user interface may include a means whereby an operator may activate or deactivate the concrete vibrator 100, for example, the user interface 113, 150 may include one or more buttons, dials, or switches for turning the motor pod 109 on or off. The user interface may also include a means for an operator to adjust the operation of the concrete vibrator 100. For example, the user interface 113, 150 may include buttons, dials, slides, switches, or other controls, that permit the operator to adjust an operating characteristic of the motor pod 109 to change the vibration imparted by the vibratory head 104 coupled thereto.

The user interface may also include one or more indicators (not illustrated). Such indicators may be light emitting diodes (LEDs) or other types of visual indicators, or may include a screen capable 152 of providing visual feedback via text or graphics. The user interface may also be configured to provide audible indicators via a speaker (not illustrated).

The motor pod 109 may include a variable speed motor, or it may include a constant speed motor. Where the motor pod 109 includes a variable speed motor, the user interface 113, 150 may include an input (e.g., a switch, dial, slider, etc.) that affects the voltage supplied to the variable speed motor, such that the operator may adjust the speed output of the variable speed motor by changing or adjusting the input. For example, the user interface may include a dial that is engagable by the operator to change the variable speed motor's output speed between two (2) or more different speed settings. The motor pod is connected to a power source (not illustrated), such as a battery pack that may be removable or an external power supply, or to an outlet via a power cord 119 operatively extending from the motor assembly 108. The motor pod 109 may also be connected to a control circuitry/PC board 125 in the form of analog or digital input signals.

With reference to FIGS. 1-4, the testing apparatus 100 further includes a frame assembly 120 configured to support the vibrator 106. The frame assembly 120 includes a plurality of legs 122 and a slider plate 124. The legs 122 are each rotatably and adjustably coupled to the slider plate 124. The legs 122 may be telescoping members configured to expand and retract. The legs 122 each include an upper end 123 that is rotatably attached to the slider plate 124 and a lower end 127 rotatably attached to a foot 126. The upper ends 123 of the legs 122 are interconnected to each other via the slider plate 124, and the lower ends 127 of the legs 122 may be interconnected to each other via a plurality of support members 128. In the illustrated example, the support members 128 are connected to the feet 126 and provided between neighboring legs 122 to thereby interconnect the bottom ends thereof.

In some embodiments, the legs 122 are spaced apart and arranged as a tripod configuration. It is to be appreciated that while a tripod arrangement of legs is shown, other configurations may be substituted herein with departing from the disclosure. For example and without limitation, the frame assembly 120 may include more than three legs 122, e.g., four legs.

The slider plate 124 is configured to permit relative sliding between it and the vibrator 106. For example, the slider 124 may have a plurality of apertures 129 sized and placed to retain at least a portion of the motor assembly 108 and cage assembly 107. In this manner, the slider 124 may be stationary and positioned to suspend the vibrator 106 with the bottom end 110*a* positioned proximate to the slider plate 124, and then unfastened from the frame 120 such that the vibrator 106 is permitted to slide within the apertures 129 in the slider plate 124 such that the top end 110*b* moves towards the slider plate 124. In some examples, at least a portion of the frame 120 includes markings for visual measurement/recording of the movement of the vibrator 104 portion relative to a sample.

The illustrated embodiments, the apertures 129 of the slider plate 124 are configured to slidingly receive the handles 114 of the cage assembly 107. The slider plate 124 may also include a central bore 133 configured to sliding receive the motor assembly 108. In some embodiments, the central bore 133 includes least one notch 135 configured to receive a correspondingly shaped at least one tab portion 115 positioned vertically along the motor assembly 108. The at least one a tab portion 115 and notch 135 may provide alignment between the vibrator and plate 124 and allow the vibrator 106 to be guided during vertical movement.

A fastener assembly may be provided on the slider plate 124, which is configured to couple the floating vibrator 106 to the frame assembly 120. The fastener assembly may also be configured to be manipulated and thereby decouple the vibrator 106 from the frame assembly 120, such that the vibrator 106 may move relative to the slider plate 124 and frame assembly and descend into the concrete test mixture as fast as the resistance of the concrete allows it.

Figure 3:
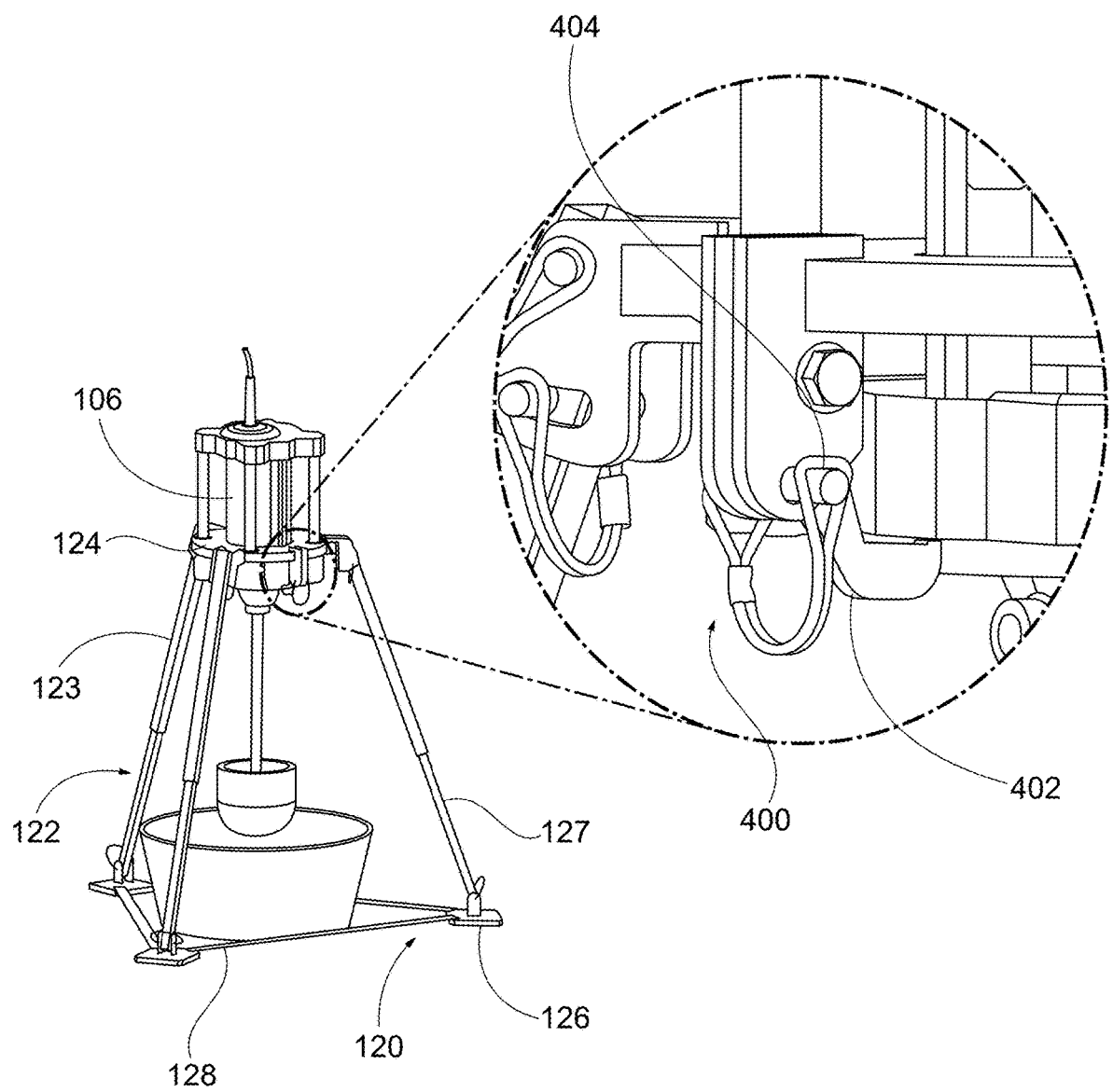
FIG. 3 is an example locking system utilizable with a concrete workability meter.
Figure 4:
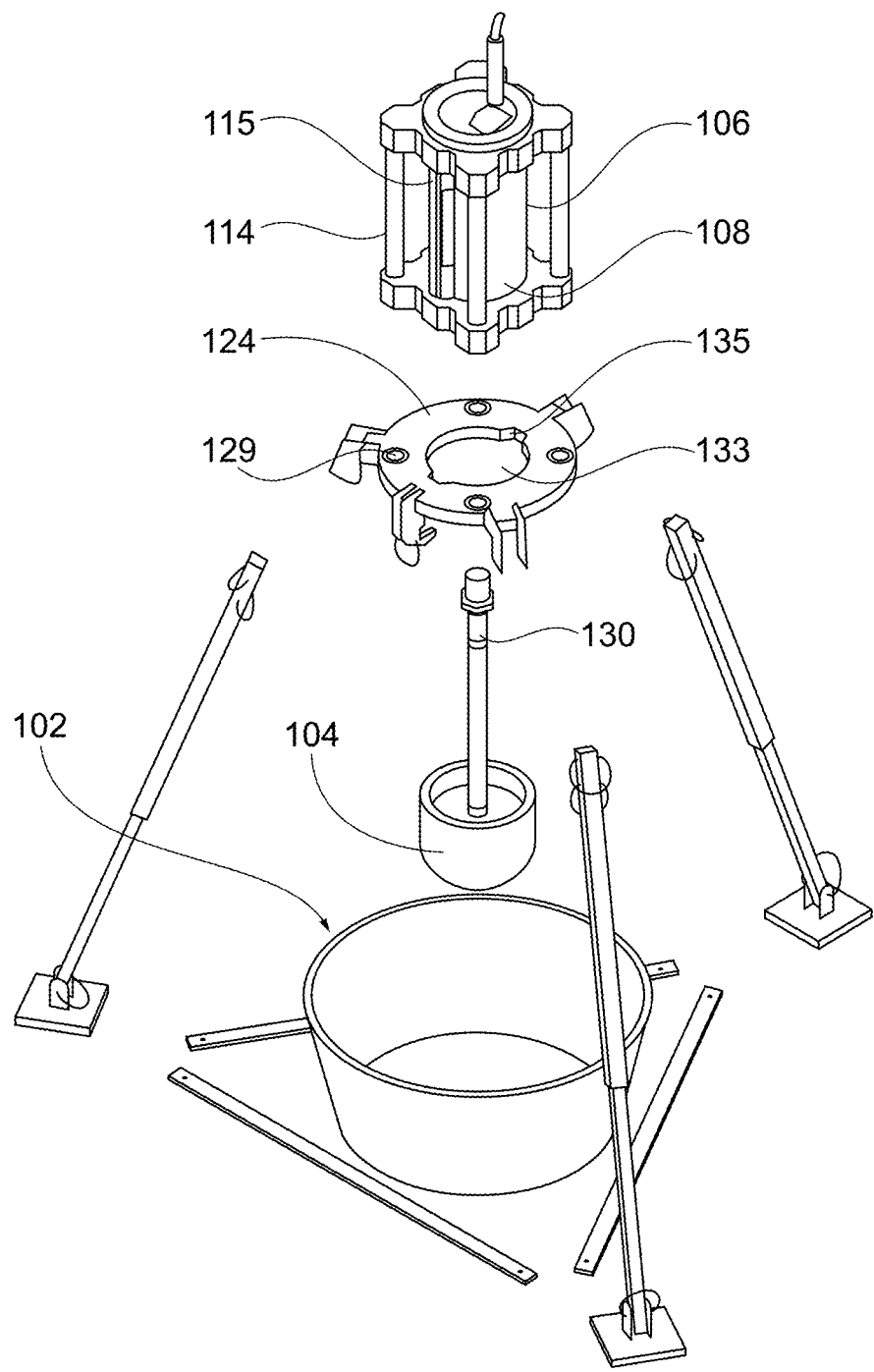
FIG. 4 is an exploded view of the concreate workability meter of FIG. 1.

FIGS. 3 and 4 illustrate an example locking system 400, wherein the locking system 400 includes a hook 402 and a pin 404. The hook 402 may be locked into an engaged position (illustrated), where the hook 402 may couple the vibrator 106 and the frame assembly 120 relative to each other, but the pin 404 may be removed to allow the hook 402 to be moved into a disengaged position where the vibrator 106 and the frame assembly 120 are not secured relative to each other to thereby permit relative movement between them.

In the illustrated example, the vibrator 106 and VKelly instrument 104 are capable of floating in position above (or relative to) the container 102. During a test, for example, the vibrator 106 and VKelly instrument 104 may descend (move) towards the container 102 via the frame assembly 120. The testing apparatus 100 may be configured such that the frame assembly 120 controls the descent (movement) of the vibrator 106 and VKelly instrument 104, for example, during a testing procedure.

In one example, the motor assembly 108 includes a PC board 125 frequency controlled motor is operatively coupled to the shaft 130 of the VKelly instrument 104 and the shaft 130 transfers vibrating energy from the motor 109 to the load sensing ball of the VKelly instrument 104. In such examples, the VKelly instrument 104 may be designed with a particular shape and known (pre-calculated) contact area. In the illustrated example, the VKelly instrument 104 is shaped with a spherical surface configured to contact the test sample. The load sensing ball may be lowered down to just above the surface of a set volume concrete sample's surface (e.g., in the container 102). The motor 109 is then turned on and a pin of the VKelly instrument 104 releases the load-sensing ball, and it sinks into the concrete sample under its own specified weight. The PC board 125 reporting electronics are accessible on remote or mobile device 150, such as a smartphone, tablet, or computer, e.g., via an application on an iOS or Android device.

The frame assembly 120 is used to hold the floating portion of the test apparatus vertically stable in the test frame as the VKelly instrument 104 descends into the concrete sample. In some embodiments, one of the motor's handles/frame tubes 108 includes a printed scale for manually observing data.

Figure 5A:
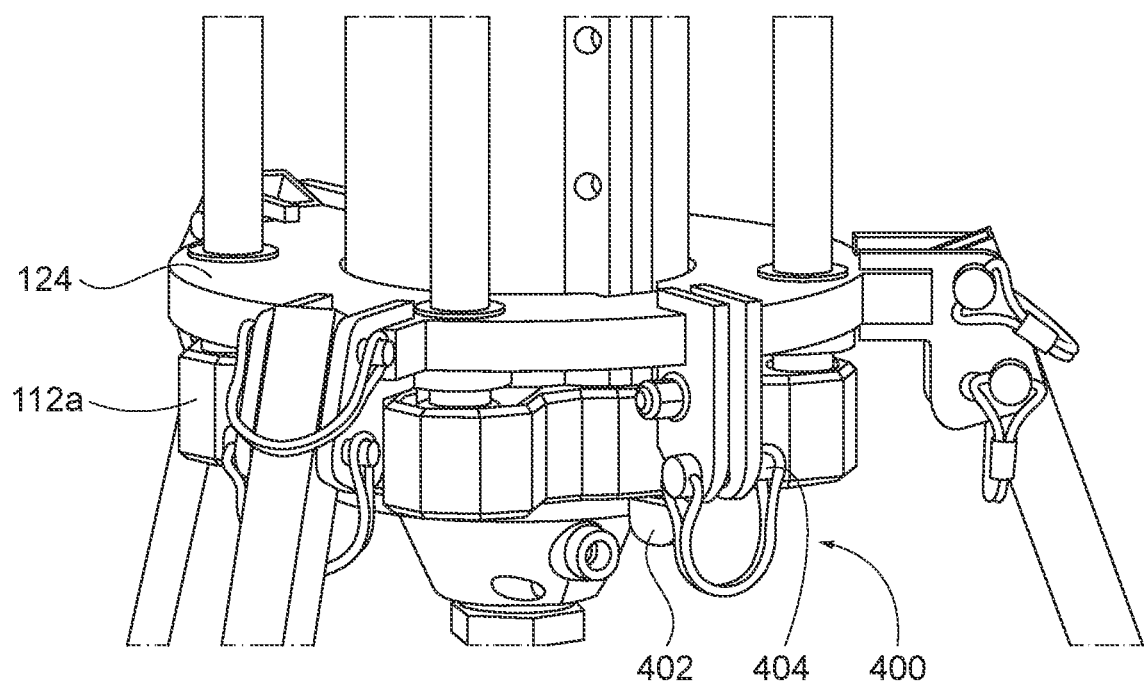
FIGS. 5A-5C illustrate example operation of concrete workability meter.
Figure 5B:
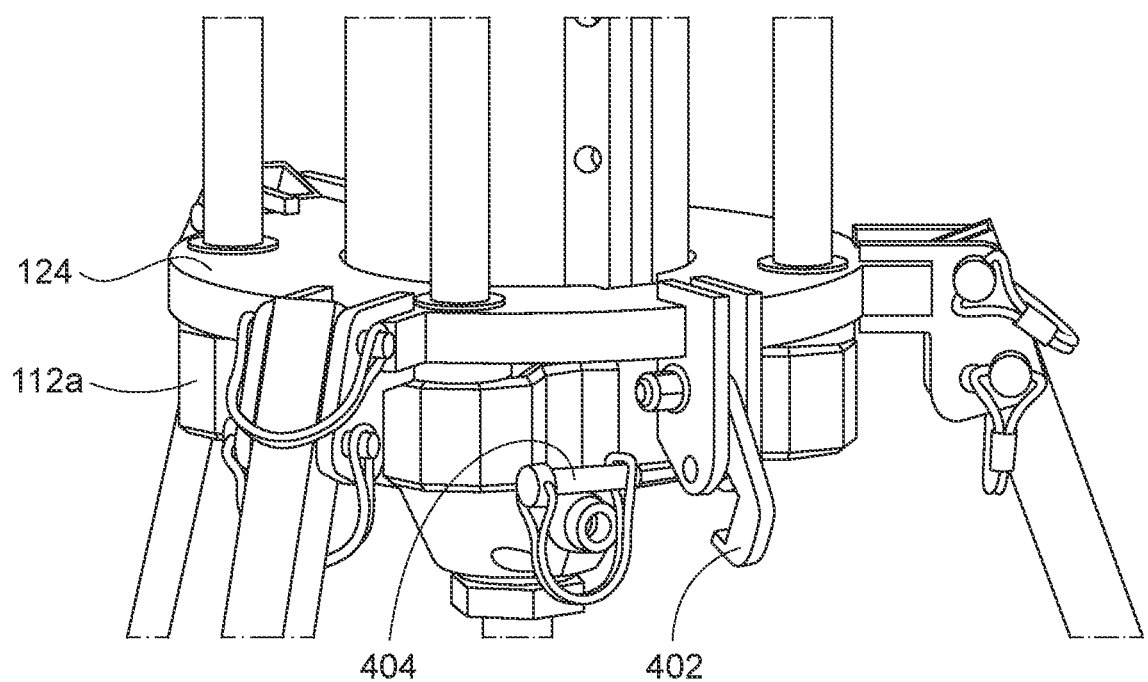
Figure 5C:
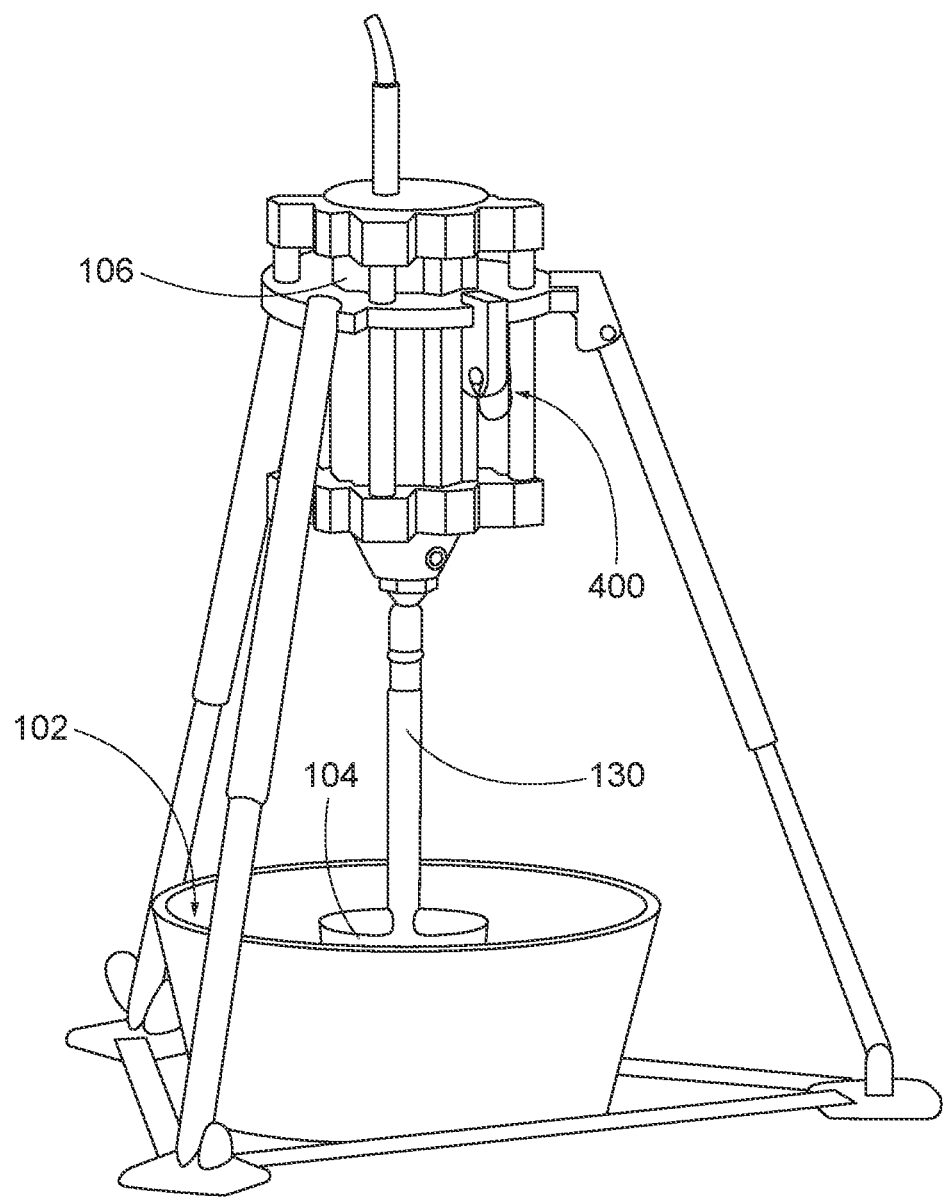

FIGS. 5A-5C illustrate an exemplary method of operation of the workability meter 100 and corresponding locking system 400. In FIG. 5A, the hook 402 may is in an engaged position where the hook 402 couples the vibrator 106 and the frame assembly 120 relative to each other. As illustrated the hook 402 is engaged with the endcap 112a preventing the vibrator 106 from vertically sliding relative to the slider plate 124. The hook 402 is prevented from disengaging with the endcap 112a due to the presence of the pin 404.

As illustrated in FIG. 5B, the pin 404 is removed to allow the hook 402 to be moved into a disengaged position where the vibrator 106 and the frame assembly 120 (via plate 124) are not secured relative to each other to thereby permit relative movement between them. The vibrator 106 with attached shaft 130 and VKelly instrument 104 may vertically move under the force of gravity towards a sample placed below. FIG. 5C illustrates the vibrator 106 in a position where the VKelly instrument 104 in embedded into the sample within container 102. Disengagement of the locking system 400 allows the test apparatus of the vibrator, shaft and VKelly instrument to make a measurement on a sample.

Figure 6:
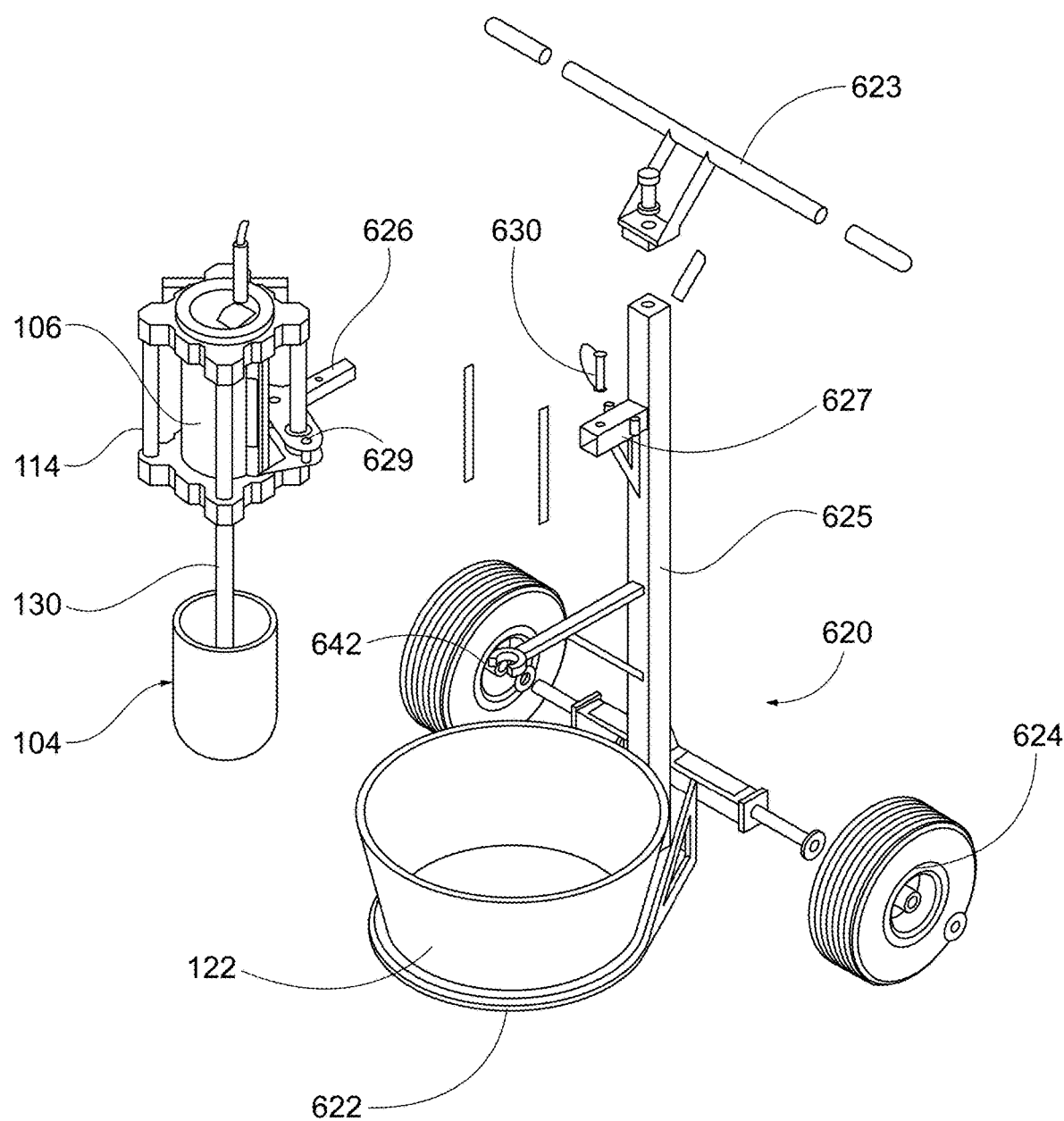
FIG. 6 is an exploded view of another concrete workability meter that may incorporate the principles of the present disclosure.
Figure 7:
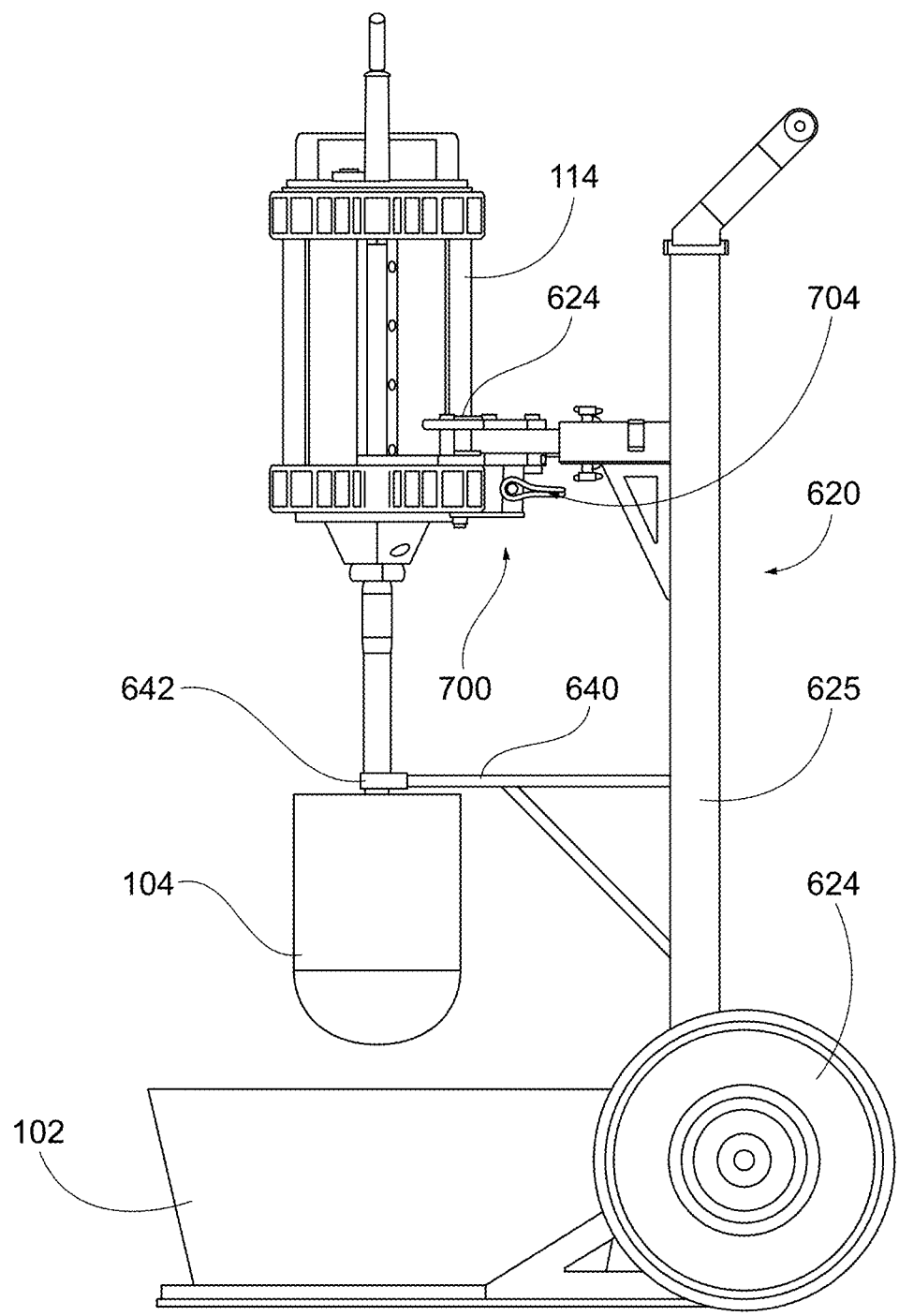
FIG. 7 is a side view of the concrete workability meter of FIG. 6.

FIG. 6 illustrates another exemplary concreate workability system in accordance with the present disclosure. The system 600 utilizes a vibrator assembly 106, shaft 130, and VKelly instrument 104 described above and best understood with reference thereto. In the embodiment, of FIG. 6, the frame 120 is replaced with a cart frame 620. The cart frame 620 includes a base 621 configured to receive and transport container 102. The cart frame 620 may be configured similar to a furniture dolly having and axle and two spaced apart wheels 624. That is, the cart frame 620 may be tilted backwards such that the base 622 is tilted off of the floor, and the cart frame 620 may be transported to a desired location by a user steering the cart frame 620 by handlebars 623.

The cart frame 620 is illustrated as having an elongated frame member 625 that extends between the handle bar 623 and base 622. The central frame member 625 may include a connection portion 627 configured to lockingly receive the vibrator assembly, including vibrator 106, shaft 130, and VKelly instrument 104 and or a sliding adaptor plate 626. In the illustrated embodiment, the sliding adaptor plate 626 includes a connector configured to engage the connection portion 627. The connection portion 627 may be a hollow tube and the connector may be a correspondingly shaped tube member configured to slidingly engage the hollow tube. A pin and/or other locking element 630 may removably secure the vibrator and/or sliding adaptor plate 626 to the cart frame 620 via connection portion 627.

In some embodiments, the sliding adaptor plate 626 includes apertures 629 configured to slidingly receive at least one handles 114 of the cage assembly 107. In this manner, the sliding adaptor plate 626 may be stationary and positioned to suspend the vibrator 106 with the bottom end 110a positioned proximate to the sliding adaptor plate 626, and then unfastened from the cart frame 620 such that the vibrator 106 is permitted to slide within the apertures 629 in the sliding adaptor plate 626 such that the top end 110b moves towards the sliding adaptor plate 626. In some examples, at least a portion of the frame 620 includes markings for visual measurement/recording of the movement of the vibrator 104 portion relative to a sample in container 102.

Similar to the embodiment of FIGS. 1-5, a fastener assembly 700 is configured to maintain a position of the vibrator 106 with respect to the sliding adaptor plate and cart frame 620. The fastener assembly 700 includes an engaged position held in place by a retention member, such as pin 704. Removal of the retention member 704 causes the fastener assembly 700 to disengage the vibrator or frame assembly 107 allowing vertical sliding movement thereof.

In some embodiments, the cart frame 620 includes a shaft guide 640 for guiding the shaft 130 during vertical sliding movement in relation thereto. The shaft guide 620 may include an end portion 642 including an aperture/complement shape (such as a C-shape) or the like to slidlingy guide the shaft 130.

The devices of FIGS. 1-7 are configured to allow a concreate workability meter to be mounted to a frame (120, 620) and then disengaged with the frame for guided vertical movement to engage a sample (the instrument 104 making contact with a sample). The devices described above are able to make measurements of the workability of a concrete sample by determining certain characteristics. In some embodiments, data related to the workability is recorded and stored, for example, by components on the PC Board 125 or via remote device 150.

Since a concrete vibrator does not exhibit a uniform product across industry manufacturers, a compact and frequency-controlled floating test portion (vibrator 106, shaft 130, instrument 104) is used to measure the load against the PC Board 125 looping system that maintains a programmed frequency to capture and report the variance in applied voltage against concrete load differential. The apparatus uses a set force of 64 (+/−5) lbf at a vibration frequency of 8,000 vpm for the collection of concrete load variances. In application, the same vibration energy dynamics may be applied to every concrete sample and the total weight of the floating portion of the test apparatus may be maintained.

The electrical load impedance curve correlates to both the behavioral principles of the Bingham Model and the measurement in ASTM C 143 (slump cone) tests of the workable behavior of plastic concrete. The Bingham Model is commonly used to evaluate concrete rheology in a more complex evaluation than that of the simple slump cone test. The slump cone just shows the relationship of the static yield stress against the pressure of the sheer stress that is applied to the sample by its own weight. In the Bingham Model, the behavior principles of non-Newtonian fluids by mapping the shear thinning when energy is applied and the shear thickening when the energy is withdrawn from the concrete material. The electrical impedance load curve differentials in the slope of the descending curve as compared to the ascending maps out a behavior of the concrete materials in the concrete sample under mechanical vibration. In the load curve signature of FIG. 8, there are several other valuable relationships that can be identified in analyzing the workability properties of the concrete sample and variances through the concrete processes (i.e., the construction practices that are applied to concrete, including but not limited to batching, transport, pumping, vibration, etc.).

In most concrete placement applications, the significance of Concrete Workability is the materials ability to be placed in forms on the construction site. Overwhelmingly, this is done with using a concrete internal vibrator. So, in testing concrete workability, the obvious technology to analyze workability is electrical load impedance curves, because it correlates to the relationships of the Bingham Model at mixture design, and an easily applied form of evaluation in all the concrete processes prior to placement. The variances in the concrete workability signature curve elements show distortions that can be identified and tracked by the ability of the device impedance reporting to a cell phone or a tablet.

Figure 8:
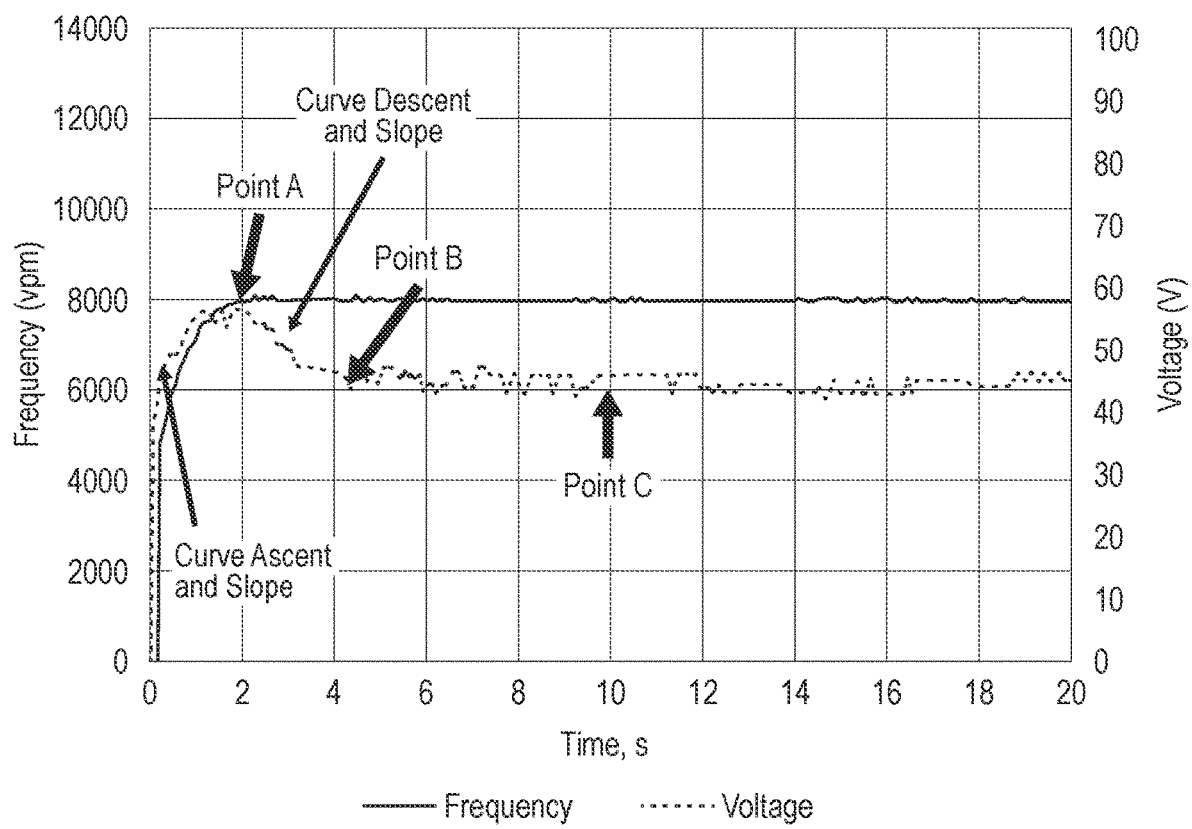
FIG. 8 is a graph of frequency and voltage vs. time.

As a controlled vibration energy (i.e., controlled frequency and set force value) is applied in lab samples, a curve is established by the interparticle friction of the concrete sample by the workability meter. FIG. 8 illustrates an example impedance curve. The impedance curve shows the necessary sheer stress over time that is needed to overcome the concrete's static yield stress value to liquefy the sample and begin reducing the particle friction (point A). This is the workability signature. The friction reduction in the curve then will bottom out at a point where the vibrator energy will begin the dynamic flow (point B). The time stamp in the curve takes out the technician's inaccuracy in manually timing a sample. The time interval from point A to point B evaluates the concrete's workability by the mixture's workability signature that is derived by multiple concrete factors contributing to particle friction. The slope of the curve's ascending slope versus the curve's descending slope is a signature that is captured in the lab that changes with addition to or subtraction of the mixture's particle friction.

The workability signature shown in FIG. 8 also includes the vibrator's change in voltage to begin (point B) dynamic flow and the voltage required to continue it for a defined time interval (point C). Both the voltage value and changes in voltage during dynamic flow are represented in the flow curve at the defined baud rate for data collection, where Baud rate is the amount of voltage changes per second. The slope of additional voltage to sustain concrete flow is the mixtures flow signature. Flow signature will show adjustments in voltage as the thixotropic behavior thickens (i.e., thickening properties as per Bingham Model) under the influence of energy.

Presently, the lack of understanding and methods of control of concrete workability is a costly practice of adjusting mixture design to compensate for construction variances. The lack of accurate, repeatable test equipment with a better graduated indexing scale leads to several identified concrete distresses. The eventual impedance curve correlation to construction practices will allow contractors to gather job data for quality Control at concrete batching through VFD at a set drum RPMs and correlation to Workability Signature curves; impedance curve signature variations of concrete pavement mixes to limit pavement surface distresses. Lower concrete break strength deviations at batching by correlated load impedance signatures; control of workability deviations during transport by site testing; limit water additions prior to concrete pumping by sensing retempering; sense workability changes in concrete workability after pumping; sense concrete workability variances that drive surface defects in vertical construction.

The present concrete workability behavior signatures for different mix proportions, fineness modules, aggregate gradations, aggregate characteristics, paste volumes, W/C, and other contributing factors that define inter-particle frictions of mixtures will have a larger data sample size to identify and verify adjustments in electrical impedance curve signatures and flow behaviors. Concrete properties and proportions are not integral to the curve signature stamps from the Concrete Workability Tester; the tester will determine the signatures of the sample. For the purposes of better or more efficient designs, concrete workability signature tracking will be useful. Since the Concrete Workability Tester uses vibration to evaluate concrete. The tester can also be used as a vibration compatibility tester.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a concrete vibrator system having vibrator portion that is positioned in a concrete mixture. The term "proximal" refers to the position of an element further away from the vibrator portion and the term "distal" refers to the position of an element closer to the vibrator portion. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To aid the Patent Office and any readers of this application and any resulting patent in interpreting the claims appended hereto, applicants do not intend any of the appended claims or claim elements to invoke 35 U.S.C. 112(f) unless the words "means for" or "step for" are explicitly used in the particular claim.

What is claimed is:

1. Concrete workability meter assembly comprising:
    a testing assembly including a concrete testing instrument operatively connected to a vibrator; and
    a frame assembly configured to slidingly support the testing assembly, wherein the frame assembly includes a slider plate configured to permit relative sliding between the slider plate and the vibrator.

2. The assembly according to claim 1, wherein the vibrator includes a variable speed motor and is controllable to manipulate the testing instrument.

3. The assembly according to claim 1 further comprising a shaft extending between the vibrator and testing instrument, the shaft configured to transfer vibrating energy from vibrator to the testing instrument.

4. The assembly according to claim 1, wherein the testing instrument is a kelly ball.

5. The assembly according to claim 1, wherein the slider plate includes a central bore includes at least one notch configured to receive a correspondingly shaped at least one tab portion positioned vertically along the vibrator, the at least one tab portion and notch configured to provide alignment and guided movement between the vibrator and slider plate.

6. The assembly according to claim 1, further comprising a cage assembly that shrouds a motor of the vibrator.

7. The assembly according claim 6, wherein the cage assembly includes a pair of endcaps and at least one handle extending therebetween wherein the at least one handle is isolated from vibrations.

8. The assembly according to claim 7 wherein the frame assembly includes a slider plate configured to permit relative sliding between the slider plate and the vibrator, the slider plate includes a plurality of apertures sized and placed to retain at least a portion of the testing assembly.

9. The assembly according to claim 1, wherein the frame assembly includes a locking system capable of having an engaged position that locks the testing assembly to the frame assembly and a disengaged position that allows sliding movement of the testing assembly relative to the frame assembly.

10. The assembly according to claim 9, wherein the locking system includes a hook configured to couple the vibrator and the frame assembly relative to one another.

11. The assembly according to claim 1, wherein the frame assembly includes a plurality of legs rotatably and adjustably coupled to a slider plate.

12. The assembly according to claim 1, wherein the frame assembly includes an elongated central frame member that extends between a handlebar and base.

13. The assembly according to claim 12 further comprising at least two wheels axially coupled to the elongated central frame member proximate to the base.

14. The assembly according to claim 1, wherein the frame assembly includes a shaft guide having an end portion configured to slidingly engage a shaft that connects the vibrator to the testing instrument.

15. The assembly according to claim 1, wherein the vibrator generates an electrical load impedance curve from a looping circuit.

16. A method of testing concrete workability, comprising:
    providing a testing apparatus having a concrete vibrator portion and frame assembly, wherein the frame assembly slidably supports the concrete vibrator portion, and the concrete vibrator portion is slidable relative to the frame assembly, and
    decoupling the concrete vibrator portion from the frame assembly to permit relative movement there between.

17. The method of claim 16, wherein the step of decoupling includes removing a pin from a hook assembly and articulating a hook into a disengaged position.

18. The method of claim 16, wherein the testing apparatus includes a vibrating source that develops an electrical load impedance curve from a looping circuit in a PC Board of the vibrating source.

19. A concrete workability meter assembly comprising:
    a testing assembly including a concrete testing instrument operatively connected to a vibrator; and
    a frame assembly configured to slidingly support the testing assembly, wherein the frame assembly is configured to permit relative sliding between the frame assembly and the vibrator.

* * * * *